US00PP24846P2

(12) United States Plant Patent
Jones

(10) Patent No.: US PP24,846 P2
(45) Date of Patent: Sep. 2, 2014

(54) ***SCAVEOLA* PLANT NAMED 'SSCSB01-0'**

(50) Latin Name: *Scaveola aemula*
Varietal Denomination: SSCSB01-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 80 days.

(21) Appl. No.: 13/694,341

(22) Filed: Nov. 20, 2012

(51) Int. Cl.
*A01H 5/00* (2006.01)

(52) U.S. Cl.
USPC ..... Plt./363

(58) Field of Classification Search
USPC ..... Plt./363
See application file for complete search history.

*Primary Examiner* — Annette Para
(74) *Attorney, Agent, or Firm* — Cassandra Bright

(57) ABSTRACT

A new and distinct *Scaveola* cultivar named 'SSCSB01-0' is disclosed, characterized by a naturally dwarf plant that remains compact in warm weather as well as remaining compact as it ages. The new variety is a *Scaveola*, normally produced as an outdoor garden or container plant.

1 Drawing Sheet

Latin name of the genus and species: *Scaveola aemula.*
Variety denomination: 'SSCSB01-0'.

BACKGROUND OF THE INVENTION

The new *Scaveola* cultivar is a product of a planned breeding program conducted by the inventor, Steve Jones, in a commercial greenhouse in Oxnard, Calif. The objective of the breeding program was to produce new *Scaveola* varieties that remain compact in warm weather.

The new variety originated as a seedling from the open pollination of various, *Scaveola aemula*, varieties. Most varieties were unnamed and unpatented however, one of the varieties used was *Scaveola aemula* 'Blue Wonder', U.S. Plant Pat. No. 7,929. The actual seed parent is unknown as seed was bulk harvested from the collection of *Scaveola* plants. The open pollination resulting in the bulk collected seed was organized by the inventor in a commercial greenhouse in Oxnard, Calif. in 2008. The new variety was selected in September of 2009.

Asexual reproduction of the new cultivar 'SSCSB01-0' by vegetative cuttings was first performed during October of 2009, at a research greenhouse in a commercial greenhouse in Oxnard, Calif. Subsequent propagation has shown that the unique features of this cultivar are stable and reproduced true to type on successive generations.

SUMMARY OF THE INVENTION

The cultivar 'SSCSB01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SSCSB01-0' These characteristics in combination distinguish 'SSCSB01-0' as a new and distinct *Scaveola* cultivar:

1. Naturally dwarf plants.
2. Plants remain compact with age.
3. Plants remain compact in warm weather.

PARENT COMPARISON

Plants of the new cultivar 'SSCSB01-0' cannot be compared to either seed or pollen parent, as the exact parents are unknown. As compared to the general population of plants in the parent grouping of plants, 'SSCSB01-0' produces significantly more compact plant habits.

COMMERCIAL COMPARISON

Plants of the new cultivar are best compared to the commercial variety *Scaveola* 'Newon', U.S. Plant Pat. No. 10,584. Plants of the new variety produce smaller foliage and slightly larger flowers. Additionally, plants of the new variety are more compact, and remain more compact in high temperatures, than 'Newon'.

Plants of the new cultivar are Can also be compared to the commercial variety *Scaveola* 'Blue Fandango', U.S. Plant Pat. No. 10,201. Plants of the new variety produce slightly larger flowers, of a deeper color. Additionally, plants of the new variety are more compact, and remain more compact in high temperatures, than 'Blue Fandango'.

BRIEF DESCRIPTION OF THE PHOTOGRAPH

The accompanying photograph in FIG. 1 illustrates in full color a typical plant of 'SSCSB01-0' grown in a greenhouse, in Oxnard, Calif., in a commercial 1 gallon container. Age of the plant photographed is approximately 10 weeks from an unrooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'SSCSB01-0' plants grown in a greenhouse in Oxnard, Calif. The growing temperature ranged from 20° C. to 28° C. The greenhouse is un-shaded, giving bright, normal sunlight conditions. Measurements and numerical values represent averages of typical plant types.

Botanical classification: *Scaveola aemula* cultivar 'SSCSB01-0'.

PROPAGATION

Time to initiate roots: About 5-8 days at approximately 20° C.

Root description: Fine, densely fibrous.

PLANT

Growth habit: Creeping, outwardly spreading annual.

Pot size of plant described: 1 gallon pot.

Height: Approximately 14 cm to top of foliage. Approximately 21 cm to top of flowering plane. Measured from soil level of pot.

Plant spread: Approximately 45 cm.

Growth rate: Rapid.

Branching characteristics: Moderately well branched. Approximately 6 to 10 primary branches per plant.

Length of primary lateral branches: Approximately 17 cm.

Diameter of lateral branches: Approximately 0.4 cm.

Quantity of lateral branches: About 20 to 30.

Stem:

*Color*.—Near RHS Green 137A, strongly overlayed with Greyed-Purple N186A.

*Texture*.—Pubescent.

Internode length: Average 2.4 cm.

Age of plant described: Approximately 10 weeks from 3 rooted cuttings.

FOLIAGE

Leaf:

*Arrangement*.—Alternate.

*Quantity*.—Approximately 6 fully expanded per main branch.

*Average length*.—Approximately 3.1 cm.

*Average width*.—Approximately 1.8 cm.

*Shape of blade*.—Spatulate.

*Apex*.—Broadly acute.

*Base*.—Attenuate.

*Attachment*.—Sessile.

*Margin*.—Entire, with 5 dentations, including apex.

*Texture of top surface*.—Scabrous.

*Texture of bottom surface*.—Softly pubescent.

*Color*.—Young foliage upper side: Near RHS Green 137A, very thin line on margin near Greyed-Purple N186B. Young foliage under side: Near RHS Green 137B, very thin line on margin near Greyed-Purple N186B. Mature foliage upper side: Near RHS Green 137A, very thin line on margin near Greyed-Purple N186B occasionally present. Mature foliage under side: Near RHS Green 137C, very thin line on margin and blotch at base near Greyed-Purple N186B occasionally present.

*Venation*.—Type: Pinnate. Venation color upper side: Near RHS Green 143C. Venation color under side: Near RHS Green 143C.

FLOWER

Natural flowering season: Flowering from early Spring through late Summer.

Inflorescence type and habit: Fan shaped single flowers single occurring from leaf axils. Clustered at terminus.

Flower longevity on plant: Individual flowers last approximately 1 week on the plant.

Quantity of flowers: Average 8 buds and 10 fully opened flowers per stem. Mature plants have approximately 80 open flowers at one time.

Individual flowers:

*Size*.—Diameter: Approximately 3.5 cm. Length: Approximately 3.5 cm. Persistence: Non-persistent. Fragrance: Faint.

*Corolla*.—Petal arrangement: 5 petals, fused from base, to approximately 50% of length, forming a half tube. Separated portion radiating into a semi-circle/fan shape. Margin: Entire. Apex: Retuse. Shape: Unfused potion, oblanceolate. Length: Unfused portion: 1.6 cm. Half Tube: 1.4 cm. Width: Unfused portion: 0.6 cm. Half Tube: 0.4 cm. Texture: Glabrous all surfaces.

*Color*.—Separate petals: When opening: Upper surface: Near RHS Violet N87A. Lower surface: Near RHS Violet 86C. Fully opened: Upper surface: Near RHS Violet 86B. Lower surface: Near RHS Violet 86D. Fading: Upper surface: Near RHS Violet 86C, center streak near Purple-Violet N80a and Violet-Blue N92A. Lower surface: Near RHS Violet-Blue 90A.

*Color*.—Half-tube: When opening: Upper surface: Near RHS Yellow-Green 150C, stripes near Violet-Blue N92A. Lower surface: Near RHS Yellow-Green 150C, stripes near Violet-Blue N92A. Fully opened: Upper surface: Near RHS Yellow 2A, stripes near Violet-Blue N92A. Lower surface: Near RHS Yellow-Green 145B, stripes near Violet-Blue N92A. Fading: Upper surface: Near RHS Yellow 3A, stripes near Violet-Blue N92A. Lower surface: Near RHS Yellow 1C, stripes near Violet-Blue N92A.

*Bud*.—Shape: Narrow conical. Length: Approximately 1.2 cm. Diameter: Approximately 0.4 cm. Color: Near RHS Green 143C.

*Calyx*.—Length: Approximately 1.4 cm. Diameter: Approximately 0.9 cm. Sepals: Quantity: 2 small and 1 larger sepal. Shape: Oblanceolate. Length: Average 0.1.1 cm. Width: Average 0.4 cm. Margin: Entire. Apex: Acute. Texture: Softly pubescent. Color: Mature: Near RHS Green 137A, apex strongly colored N186C.

*Peduncle*.—Length: Average 0.2 cm. Diameter: 0.1 cm. Color: Near RHS Green 137B. Orientation: Approximately 45 degree angle from attachment. Strength: Strong. Texture: Softly pubescent.

REPRODUCTIVE ORGANS

Stamens:

*Number*.—5.

*Filament length*.—Approximately 0.5 cm.

*Filament color*.—Near RHS Greyed-Yellow 160D.

Anthers:

*Shape*.—Elliptic.

*Length*.—Approximately 1.5 mm.

*Color*.—Near RHS Greyed-Orange 166A.

*Pollen*.—Pollen production not observed.

Pistil:

*Number*.—1.

*Length*.—Approximately 1.4 cm.

*Style*.—Length: Approximately 1.0 cm. Color: Base near White 155A, upper portion colored near Greyed-Purple N186C.

*Stigma*.—Shape: Flattened deltoid. Texture: Papillose. Hairs colored near Violet-Blue N92A. Color: Near RHS White 155C. Ovary color: Near RHS Green 143C.

OTHER CHARACTERISTICS

Seeds and fruits: Not observed to date.

Disease/pest resistance: Neither resistance nor susceptibility to pathogens and pests common to *Scaveola* have been observed.

Temperature tolerance: The new variety tolerates temperatures between 5 to 35° C.

What is claimed is:

1. A new and distinct cultivar of *Scaveola* plant named 'SSCSB01-0' as herein illustrated and described.

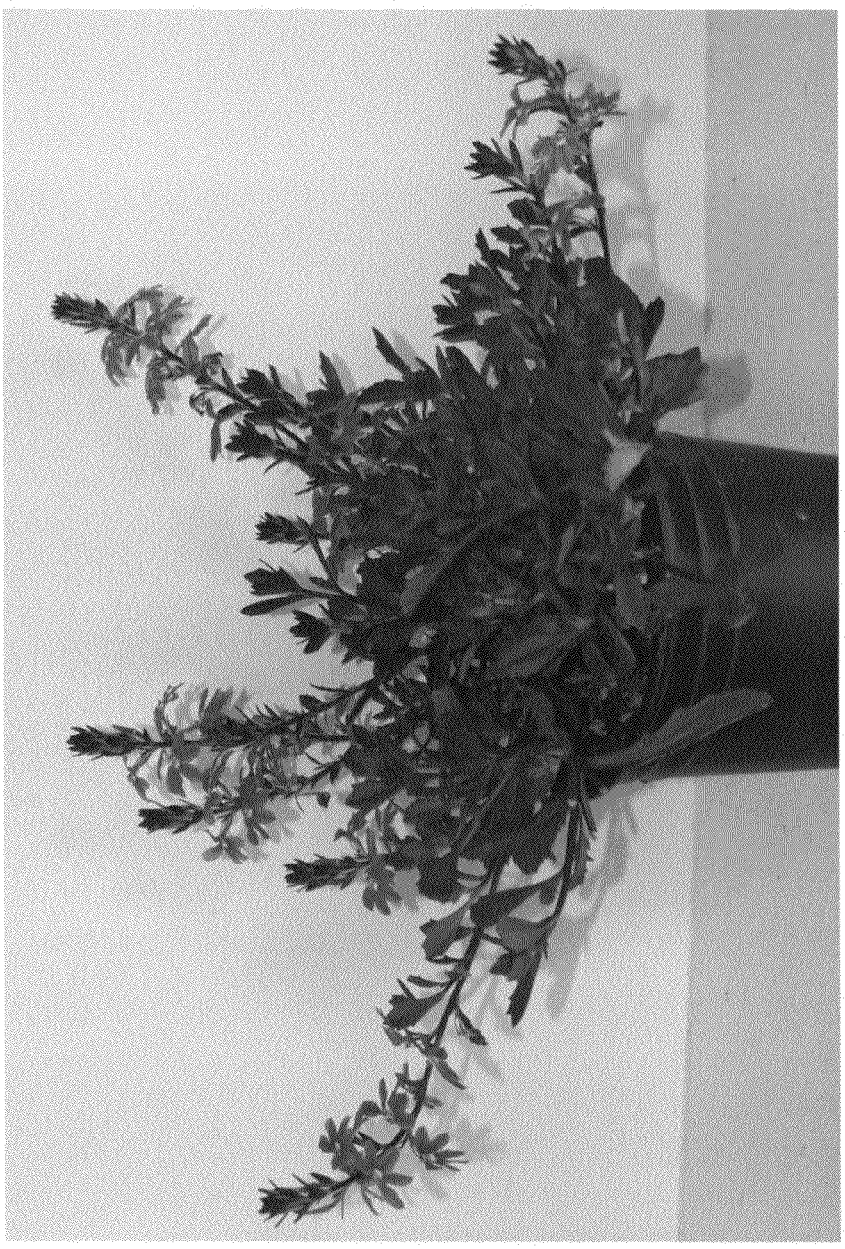

* * * * *